United States Patent
Bullock et al.

(10) Patent No.: US 6,887,743 B2
(45) Date of Patent: May 3, 2005

(54) METHOD OF FABRICATING A GATE DIELECTRIC LAYER FOR A THIN FILM TRANSISTOR

(75) Inventors: Richard Bullock, Gwent (GB); David Paul Jones, Cardiff (GB)

(73) Assignee: International Rectifier Corporation, El Segundo, CA (US)

( * ) Notice: Subject to any disclaimer, the term of this patent is extended or adjusted under 35 U.S.C. 154(b) by 0 days.

(21) Appl. No.: 09/773,872

(22) Filed: Feb. 2, 2001

(65) Prior Publication Data

US 2002/0090767 A1 Jul. 11, 2002

Related U.S. Application Data

(63) Continuation of application No. 09/488,130, filed on Jan. 20, 2000, now Pat. No. 6,223,165
(60) Provisional application No. 60/125,557, filed on Mar. 22, 1999.

(51) Int. Cl.[7] .............................................. H01L 21/84
(52) U.S. Cl. ...................................... 438/151; 438/762
(58) Field of Search ................................ 438/151–166, 438/762

(56) References Cited

U.S. PATENT DOCUMENTS

| | | | | |
|---|---|---|---|---|
| 4,675,978 A | * | 6/1987 | Swartz .............. 148/DIG. 118 |
| 4,851,370 A | * | 7/1989 | Doklan et al. ............... 257/411 |
| 5,712,208 A | | 1/1998 | Tseng et al. ................ 438/770 |
| 5,940,736 A | * | 8/1999 | Brady et al. ................ 438/762 |
| 5,981,347 A | * | 11/1999 | Kuo et al. ................... 438/308 |
| 6,040,207 A | | 3/2000 | Gardner et al. ............. 438/216 |
| 6,121,095 A | | 9/2000 | Tai et al. .................... 438/287 |
| 6,124,154 A | * | 9/2000 | Miyasaka ................... 438/149 |
| 6,124,171 A | | 9/2000 | Arghavani et al. .......... 438/286 |
| 6,124,210 A | | 9/2000 | Chino et al. ................ 438/706 |
| 6,228,751 B1 | * | 5/2001 | Yamazaki et al. ........... 134/1.2 |
| 6,281,138 B1 | * | 8/2001 | Brady et al. ............... 257/410 |
| 6,306,213 B1 | * | 10/2001 | Yamazaki ..................... 117/95 |
| 6,372,083 B1 | * | 4/2002 | Oana et al. ................. 118/695 |

* cited by examiner

*Primary Examiner*—Richard A. Booth
(74) *Attorney, Agent, or Firm*—Ostrolenk, Faber, Gerb & Soffen, LLP

(57) ABSTRACT

Methods of forming a gate dielectric layer, and a composite gate dielectric layer, for a thin film transistor, has been developed. A first embodiment of this invention describes the procedure used to create the composite gate dielectric layer. A first, thin silicon oxide gate dielectric layer is thermally grown on an underlying active semiconductor layer, such as polysilicon. A first anneal procedure, is performed at a temperature greater than the temperature used for the thermal growth of this layer, resulting in improved parametric integrity. A thicker, second silicon oxide gate dielectric layer is then thermally deposited, followed by an anneal procedure used to provide a composite gate dielectric layer comprised of a densified, thermally deposited second silicon oxide gate dielectric layer, on an underlying, thermally grown first silicon oxide gate dielectric layer. A second embodiment of this invention entails the use of the densified, thermally deposited, second silicon oxide gate dielectric layer, directly on the polysilicon, active layer.

19 Claims, 3 Drawing Sheets

METHOD OF FABRICATING A GATE DIELECTRIC LAYER FOR A THIN FILM TRANSISTOR

This application is a continuation of U.S. patent application Ser. No. 09/488,130, filed Jan. 20, 2000, now U.S. Pat. No. 6,223,165 which claims the benefit of the Provisional Application No. 60/125,557 filed on March 22, 1999, which is incorporated herein the reference.

BACKGROUND OF THE INVENTION

(1) Field of the Invention

The present invention relates to methods used to fabricate integrated circuits, and more specifically to a method used to form a gate dielectric layer for a thin film transistor.

(2) Description of Prior Art

Thin film transistors (TFT), have been used for specific integrated circuit applications. One such application for TFT devices have been in the area of liquid crystal display (LCD), panels. A transmissive-type LCD display panel comprises an array of light valves that selectively transmit incident light, in order to form an image on a display screen when the panel is backlit by a strong incandescent or fluorescent light source. Driving circuitry is provided to operate the light valves. Typically each light valve is energized by a TFT device, addressed along row and column addressing lines.

The TFT devices are comprised with a dielectric layer, used as the gate insulator layer, formed on a channel portion of an underlying active layer. For conventional metal oxide semiconductor field effect transistor (MOSFET), used for memory and logic applications, the gate insulator layer is a thin silicon dioxide layer, thermally grown on an underlying single crystalline, silicon substrate. In contrast, the gate dielectric layer used in TFT applications, is grown, or formed on an underlying active region comprised of polysilicon. Unlike single crystalline silicon, this polysilicon layer is comprised of numerous small grains which create an uneven surface. The ability to thermally grow a gate dielectric layer, with the desired integrity in terms of leakage and breakdown, is adversely influenced by the unevenness of the underlying polysilicon surface, when compared to counterpart gate dielectric layers formed on underlying single crystalline silicon surfaces. Therefore a conventional gate dielectric layer formed on this uneven polysilicon surface will give inadequate TFT parametric integrity such as low gate breakdown voltage and high gate leakage current.

The present invention will describe fabrication procedures used to improve the integrity of a gate dielectric layer, for a TFT device, formed on an underlying active layer, such as polysilicon. The present invention will feature specific growth and anneal sequences for the TFT gate dielectric layer, which have demonstrated to improve the parametric performance of the overlying gate insulator layer. The present invention will also describe a novel process sequence, used to improve the integrity of a deposited gate dielectric layer. The deposited gate dielectric layer can either be used as an overlying component of a composite gate dielectric layer, comprised of the deposited layer on the underlying thermally grown gate dielectric layer, or used as the gate dielectric layer, directly on the underlying active layer. Prior art, such as Arghavani et al, in U.S. Pat. No. 6,124,171, as well as Tai et al, in U.S. Pat. No. 6,121,095, describe methods of forming silicon dioxide gate dielectric layers on underlying single crystalline silicon substrates, however these prior arts do not describe the novel process sequence, introduced in this present invention, in which specific growth and anneal procedures are detailed for a composite gate dielectric layer, or for a thermally deposited gate dielectric layer, on an underlying, non-single crystalline, active layer.

SUMMARY OF THE INVENTION

It is an object of this invention to fabricate a thin film transistor (TFT), featuring a gate dielectric layer formed on an underlying polysilicon, active layer.

It is another object of this invention to form a gate dielectric layer on an underlying polysilicon, active layer, via thermal deposition of a silicon oxide layer, followed by an anneal cycle.

It is still another object of this invention to thermally grow a thin gate dielectric layer, on the underlying polysilicon active layer, followed by an anneal prior to thermal deposition of an overlying gate dielectric layer which has been shown to improve the TFT parametric performance.

In accordance with the present invention a method of forming a gate dielectric layer, for a TFT device, is described. An active layer of polysilicon is provided on an underlying insulator layer. For a first embodiment of this invention a thin, first dielectric layer is thermally formed, in an oxidizing ambient, on the underlying, polysilicon active layer. A first, in situ anneal cycle is then performed at a temperature greater than the temperature used for thermal growth of the thin first gate dielectric layer. An overlying, second gate dielectric layer is next thermally deposited on the underlying thin, first gate dielectric layer, with the second gate dielectric thickness adjusted to meet circuit capacitance requirements. A second in situ anneal cycle is then performed to densify the second gate dielectric layer. Deposition of an overlying polysilicon layer is followed by patterning of the polysilicon layer, and of the composite gate dielectric layer, to form the gate structure for the TFT device. Formation of a source/drain region, in an area of the polysilicon active layer, not covered by the gate structure, complete the process sequence for the TFT device.

A second embodiment of this invention entails thermal deposition of the second gate dielectric layer directly on the top surface of the polysilicon active layer. An anneal procedure is then employed for densification purposes. Deposition of an overlying polysilicon layer, and patterning of the polysilicon layer and of the second gate dielectric layer, form the desired gate structure, followed by formation of the source/drain region.

BRIEF DESCRIPTION OF THE DRAWINGS

The object and other advantages of this invention are best described in the preferred embodiments with reference to the attached drawings that include.

DESCRIPTION OF THE PREFERRED EMBODIMENTS

Figure 1:
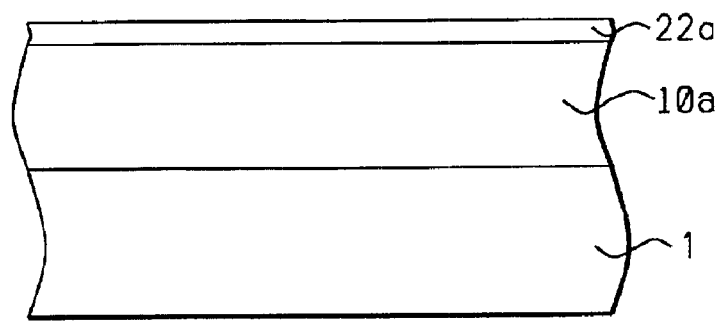
FIGS. 1–5, which schematically, in cross-sectional style, describe key stages of fabrication used to create a TFT device featuring a composite gate dielectric layer comprised of an underlying, thin thermally grown gate dielectric layer, and an overlying, thermally deposited gate dielectric layer.

The method of fabricating a gate dielectric layer, or composite gate dielectric layer, for a TFT device will now be described in detail. The TFT will be formed on an underlying insulating substrate 1. Any suitable insulating substrate may be employed, such as silicon oxide, sapphire, or preferably quartz. The first embodiment of this invention will describe a composite gate dielectric layer, comprised of an underlying, thin gate dielectric layer, thermally grown, and an overlying, thicker, gate dielectric layer, thermally deposited. The use of an underlying, thermally grown gate dielectric layer enhances the integrity of the composite gate dielectric layer, for example in terms of gate dielectric breakdown and TFT leakage characteristics, when compared to counterparts comprised with only one gate dielectric layer, thermally deposited directly on an underlying active layer. An active layer 10a, shown schematically in FIG. 1, is formed on insulating substrate 1. Active layer 10a, is a semiconductor material, such as a polysilicon layer, and is formed on insulating substrate 1, via a low pressure chemical vapor deposition (LPCVD), procedure between about 500 to 1500 Angstroms. A first, gate dielectric layer 22a, shown schematically in FIG. 1, is next thermally grown on active layer, or polysilicon layer 10a, at a temperature between about 800 to 1100° C., preferably about 900° C., in an oxidizing ambient, such as a mixture of oxygen in argon or nitrogen. The thermal oxidation procedure performed for a time between about 15 to 30 min, results in the growth of a silicon dioxide, gate dielectric layer at a thickness between about 50 to 150 Angstroms, preferably 100 Angstroms. However the many small grains, and many grain boundaries contained in polysilicon layer 10a, cause surface roughness which results in a gate dielectric layer exhibiting lower integrity in terms of dielectric breakdown voltage and leakage, than counterpart gate dielectric layers that were thermally grown on single crystalline silicon substrates, comprised without small grains and numerous grain boundaries.

Figure 2:
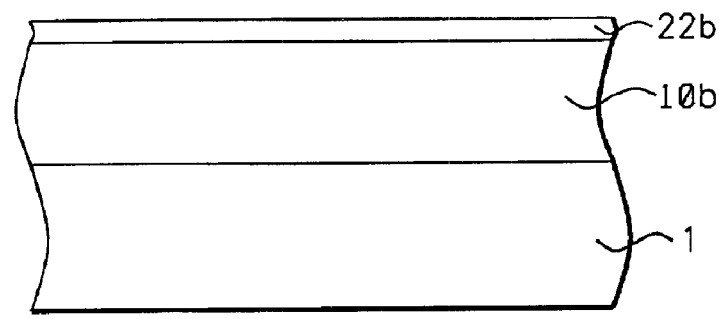

To improve TFT parametric performance, an anneal procedure is performed in an non-oxidizing ambient, resulting in active layer 10b. The anneal procedure is accomplished in situ, by increasing the temperature in the same furnace used for growth of first gate dielectric layer 22a, by an amount between about 10 to 20%. This results in an anneal temperature between about 900 to 1200° C., preferably about 1000° C. This is schematically shown in FIG. 2. An inert ambient comprised of either nitrogen or argon is used for an anneal time of about 3 to 5 hrs. The time of anneal, between about 10 to 15 times longer than the oxidation time, again results in a TFT with improved device parametric performance when compared to counterpart dielectric layers, overlying an active layer comprised with smaller grains, thus more grain boundaries.

Figure 3:
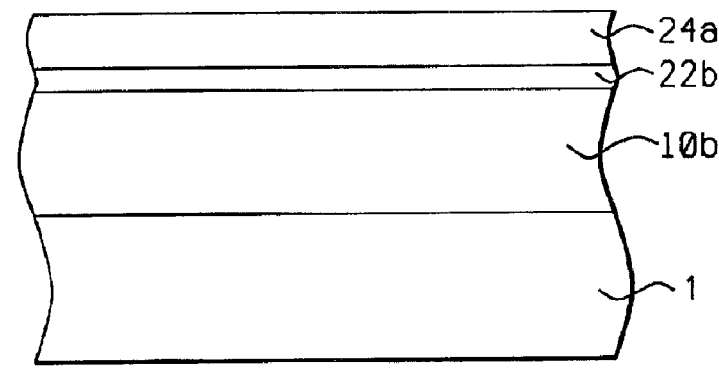
Figure 4:
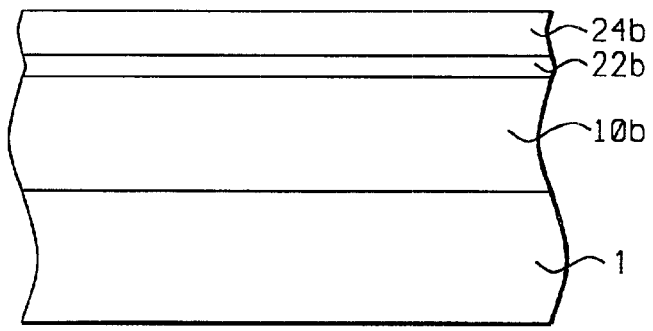

The second component of the composite dielectric layer, needed to satisfy the thickness requirement for the TFT gate dielectric layer, is next addressed and schematically described using FIGS. 3–4. A chemically vapor deposited, silicon oxide layer, is used for the thicker, second gate dielectric layer 24a. Second gate dielectric layer 24a, is obtained via thermal deposition procedures, using tetraethylorthosilicate (TEOS), as a source. Silicon oxide layers, obtained via TEOS thermally deposition procedures, have produced silicon oxide layers exhibiting greater uniformity when compared to silicon oxide layers obtained via plasma enhanced chemical vapor deposition (PECVD), TEOS procedures. Second gate dielectric layer 24a, is deposited to a thickness between about 500 to 700 Angstroms, to bring the total thickness of the composite dielectric layer to between about 550 to 850 Angstroms. Second gate dielectric layer 24a, shown schematically in FIG. 3, is thermally deposited at a temperature between about 600 to 700° C. To decrease porosity in the as deposited, second gate dielectric layer 24a, an anneal cycle is performed at a temperature between about 900 to 1000° C., in an ambient comprised of a mixture of argon or nitrogen, and oxygen. The annealing of second gate dielectric layer 24a, results in the creation of second gate dielectric layer 24b, comprised with less porosity, and improved device parametric performance, when compared to unannealed counterparts. The result of this procedure is schematically shown in FIG. 4.

Figure 5:
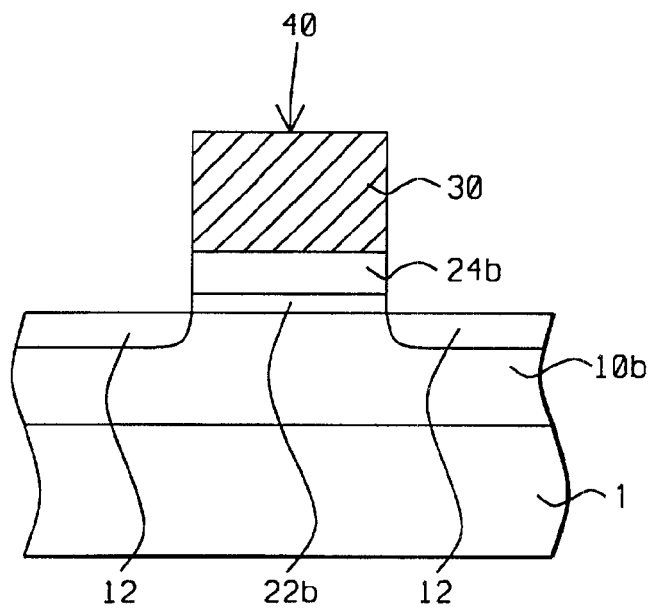

The completion of the TFT device is next addressed and schematically shown in FIG. 5. A polysilicon layer 30, is deposited via low pressure chemical vapor deposition (LPCVD), procedures, to a thickness between about 3000 to 5000 Angstroms. Polysilicon layer 30, is either doped in situ, during deposition, via the addition of arsine or phosphine, to a silane ambient, or polysilicon layer 30, or externally doped in a diffusion tube by the use of $PH_3$ or $POCl_3$ gas sources, or polysilicon layer 30, is deposited intrinsically then doped via implantation of arsenic or phosphorous ions. Conventional photolithographic and reactive ion etching (RIE), procedures, are then employed to pattern polysilicon layer 30, second gate dielectric layer 24b, and first gate dielectric layer 22b, creating gate structure 40. The RIE procedure used for definition of gate structure 40, employs $Cl_2$ or $SF_6$ as a selective etchant for polysilicon layer 30, while $CHF_3$ or $CF_4$ is used as an etchant for the gate dielectric layers, selectively terminating at the appearance of active layer 10b. After removal of the photoresist shape, used to define gate structure 40, source drain region 12, is formed in a region of active layer 10b, not covered by gate structure 40, via implantation of arsenic, or phosphorous ions, at an energy between about 50 to 100 KeV, and at a dose between about 1E15 to 1E16 atoms/$cm^2$. Subsequent processing steps used to produce a final TFT device, such as the addition of metal interconnect structures, and passivation layers, familiar to those skilled in the art, will not be described in detail here.

Figure 6:
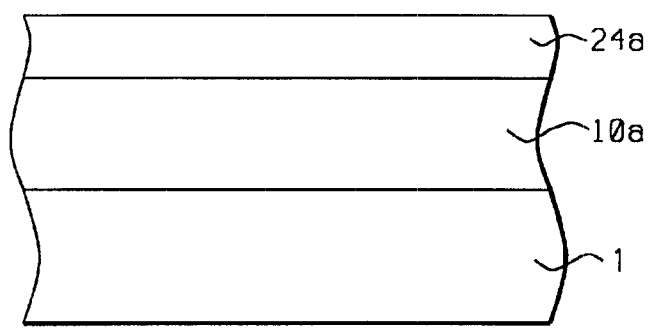
FIGS. 6–8, which schematically, in cross-sectional style, describe key stages of fabrication used to create a TFT device featuring a gate dielectric layer obtained via thermal deposition procedures.
Figure 7:
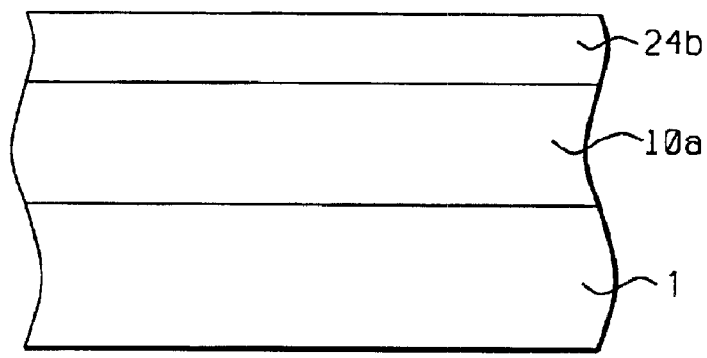

A second embodiment of this invention, featuring the use of a single, gate dielectric layer, is now described. Deposition of active layer, or polysilicon layer 10a, using identical conditions previously described in the first embodiment, is again used. A thermally deposited, gate dielectric layer 24a, obtained using TEOS as a source, is formed on active layer 10a, at a thickness between about 300 to 900 Angstroms, preferably 600 Angstroms, again using conditions identical to conditions previously used in the first embodiment, for deposition of second gate dielectric layer 24a. This is schematically shown in FIG. 6. To improve the density of the as deposited, gate dielectric layer 24a, an anneal procedure is performed, again using the identical anneal procedures applied to second gate dielectric layer 24a, in the first embodiment. The result of this anneal procedure is the creation of second, gate dielectric layer 24b, shown schematically in FIG. 7, on active layer 10a. An anneal procedure, previously applied to active layer 10a, in the first embodiment, could be used if required in the second embodiment even though a thermally grown, first gate dielectric layer is not used. The conditions of this anneal are identical to those described in the first embodiment.

Figure 8:
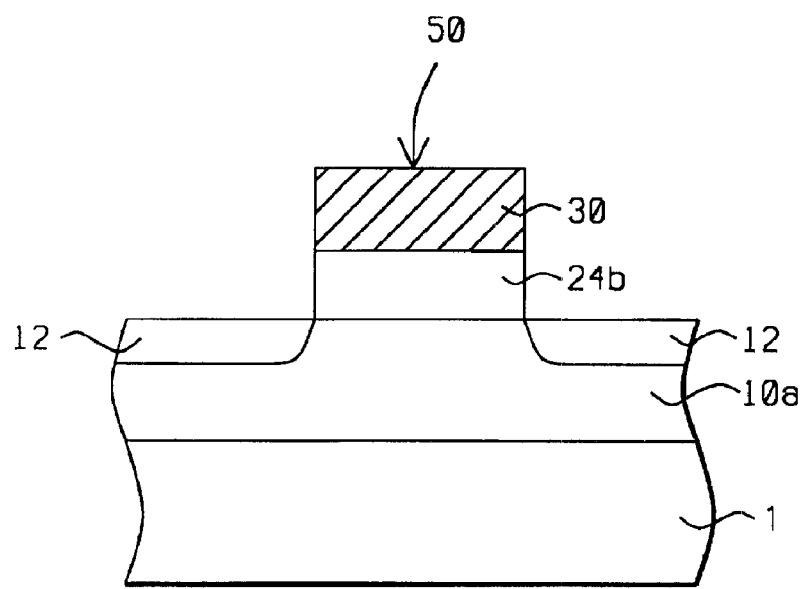

Gate structure 50, comprised of polysilicon layer 30, and second gate dielectric layer 24b, is next performed, using conventional photolithographic and RIE procedures, again using $Cl_2$ or $SF_6$ as an etchant for polysilicon, while using $CHF_3$ or $CF_4$ as an etchant for second gate dielectric layer 24b. Source/drain region 12, is again formed in regions of active layer 10a, not covered by gate structure 50. The result of these procedures are schematically shown in FIG. 8. The use of only a single, thick, gate dielectric layer, illustrated in the second embodiment, offers reduced process complexity when compared to the composite, gate dielectric layer, featured in the first embodiment. However the composite gate dielectric layer, featuring the use of the thermally grown, underlying dielectric component, provides improved device parametric performance, when compared to TFT devices comprised with only a single, thermally deposited, gate dielectric layer.

While this invention has been particularly shown and described with reference to, the preferred embodiments thereof, it will be understood by those skilled in the art that various changes in form and details may be made without departing from the spirit and scope of this invention.

What is claimed is:

1. A method of forming a composite gate dielectric layer for a thin film transistor (TFT), device, comprising the steps of:
   providing an insulating substrate;
   providing a rough polysilicon layer on said insulating substrate;
   thermally growing a first gate dielectric layer, in a furnace, on said polysilicon layer;
   subsequent to growing said first gate dielectric layer, performing a first anneal procedure to change said polysilicon layer;
   thermally depositing a second gate dielectric layer on said first gate dielectric layer; and
   performing a second anneal procedure to create a densified second gate dielectric layer, resulting in said composite gate dielectric layer comprised of said densified second gate dielectric on said first gate dielectric layer, said composite gate dielectric layer having a thickness of from about 550 to 850 Angstroms.

2. The method of claim 1, wherein said polysilicon layer is obtained via low pressure chemical vapor deposition (LPCVD) procedures to a thickness of from about 500 to 1000 Angstroms.

3. The method of claim 1, wherein said first gate dielectric layer is a silicon oxide layer, at a thickness between about 50 to 150 Angstroms, obtained via thermal oxidation procedures, performed in an ambient comprised of a mixture of oxygen in either argon or nitrogen, at a temperature between about 800 to 1100° C., and performed for a time between about 15 to 30 mm.

4. The method of claim 1, wherein said first anneal procedure, used to change said polysilicon layer, is performed at a temperature between about 900 to 1200° C., in a nitrogen or argon ambient, for a time between about 3 to 5 hrs.

5. The method of claim 1, wherein said second gate dielectric layer is a thermally deposited silicon oxide layer, obtained at a thickness between about 500 to 700 Angstroms, deposited at a temperature between about 600 to 700° C., using tetraethylorthosilicate as a source.

6. The method of claim 1, wherein said second anneal procedure, used to create said densified second gate dielectric layer, is performed at a temperature between about 900 to 1000° C., in an ambient comprised of a mixture of oxygen in either nitrogen or argon.

7. A method forming a thin film transistor, featuring a composite gate dielectric layer, on an insulating substrate, comprising the steps of:
   providing said insulating substrate;
   forming a first rough polysilicon layer on said insulating substrate;
   thermally growing a first silicon oxide layer, in a furnace, on said polysilicon layer;
   subsequent to growing said first silicon oxide layer, performing a first anneal procedure, in situ in said furnace, to improve TFT parametric performance;
   thermally depositing a second silicon oxide gate dielectric layer, on underlying, said first silicon oxide dielectric layer, via thermal decomposition of tetraethylorthosilicate (TEOS),
   performing a second anneal procedure to densify said second silicon oxide gate dielectric layer, resulting in said composite gate dielectric layer, comprised of densified, said second silicon oxide gate dielectric layer on said.first silicon oxide gate insulator layer, said composite gate dielectric layer having a thickness of from about 550 to 850 Angstroms;
   depositing a second polysilicon layer;
   patterning of said second polysilicon layer, and of said composite gate dielectric layer to create a polysilicon gate structure on said composite gate dielectric layer; and
   forming a source/drain region in a portion of said first polysilicon layer, not covered by said polysilicon gate structure.

8. The method of claim 7, wherein said first polysilicon layer is obtained via low pressure chemical vapor deposition (LPCVD) procedures, to a thickness between about 500 to 1500 Angstroms.

9. The method of claim 7, wherein said first silicon oxide gate dielectric layer is thermally grown to a thickness between about 50 to 150 Angstroms, via thermal oxidation procedures performed in an ambient comprised of a mixture of oxygen in either argon or nitrogen, at a temperature between about 800 to 1100° C., and for a time between about 15 to 30 mm.

10. The method of claim 7, wherein said anneal procedure, used to improve TFT parametric performance, is performed at a temperature between about 900 to 1200° C., in a nitrogen or argon ambient, for a time between about 3 to 5 hrs.

11. The method of claim 7, wherein said second silicon oxide gate dielectric layer is a thermally deposited silicon oxide layer, obtained at a thickness between about 500 to 700 Angstroms, deposited at a temperature between about 600 to 700° C., using tetraethylorthosilicate as a source.

12. The method of claim 7, wherein said second anneal procedure, used to densify said second silicon oxide gate dielectric layer, is performed at a temperature between about 900 to 1000° C., in an ambient comprised of a mixture of oxygen, in either nitrogen or argon.

13. The method of claim 7, wherein said second polysilicon layer is obtained via low pressure chemical vapor deposition (LPCVD), procedures, at a thickness between about 3000 to 5000 Angstroms, and either doped in situ, during deposition, via the addition of arsine, or phosphine, to a silane ambient, or doped using $PH_3$ or $POCl_3$ source in a diffusion tube, or deposited intrinsically then doped via implantation of arsenic or phosphorous ions.

14. The method of claim 7, wherein said polysilicon gate structure, on said composite gate dielectric layer, is formed via a reactive ion etching procedure, using $Cl_2$ or $SF_6$ as an etchant for said second polysilicon layer, while using $CF_4$ or $CHF_3$ as an etchant for said composite gate dielectric layer.

15. The method of claim 7, wherein said source/drain region is formed via implantation of arsenic or phosphorous ions, at an energy between about 50 to 100 KeV, at a dose between about 1E15 to 1E16 atoms/cm$^2$.

16. A method of forming a thermally deposited, gate dielectric layer, for a thin film transistor device, comprising the steps of:

providing an insulating substrate;

forming a rough polysilicon layer on said insulating substrate;

thermally depositing a silicon oxide gate dielectric layer on said polysilicon layer, using tetraethylorthosilicate as a source to a thickness of from about 500 to 700 Angstroms; and performing an anneal procedure to densify said silicon oxide gate dielectric layer.

17. The method of claim 16, wherein said polysilicon layer is obtained via low pressure chemical vapor deposition (LPCVD) procedures to a thickness of from about 500 to 1500 Angstroms.

18. The method of claim 16, wherein said silicon oxide gate dielectric layer is deposited at a temperature between about 600 to 700° C.

19. The method of claim 16, wherein said anneal procedure, used to densify said silicon oxide gate dielectric layer, is performed at a temperature between about 900 to 1000° C., in an ambient comprised of a mixture of oxygen in either nitrogen or argon.

* * * * *

UNITED STATES PATENT AND TRADEMARK OFFICE
CERTIFICATE OF CORRECTION

PATENT NO. : 6,887,743 B2 Page 1 of 1
DATED : May 3, 2005
INVENTOR(S) : Richard Bullock and David Paul Jones It is certified that error appears in the above-identified patent and that said Letters Patent is hereby corrected as shown below:

<u>Title page,</u>
Item [75], Inventor, change to -- Richard Bullock, Newport (GB) --.

Signed and Sealed this

Fifth Day of July, 2005

JON W. DUDAS
*Director of the United States Patent and Trademark Office*